United States Patent
Goulding et al.

(10) Patent No.: US 6,974,607 B2
(45) Date of Patent: Dec. 13, 2005

(54) PYRANS AS LIQUID CRYSTALS

(75) Inventors: Mark John Goulding, Ringwood (GB);
Warren Duffy, Southampton (GB);
Kevin Adlem, Bournemouth (GB);
Peer Kirsch, Seeheim-Jugenheim (DE);
Alexander Hahn, Rüsselsheim (DE);
Eike Poetsch, Mühltal (DE); Werner
Binder, Dieburg (DE); Volker Meyer,
Gross-Zimmern (DE); Melanie
Klasen-Memmer, Heuchelheim (DE);
Michael Heckmeier, Hemsbach (DE);
Georg Lüssem, Petershausen (DE)

(73) Assignee: Merck Patent GmbH, Darmstadt (DE)

( * ) Notice: Subject to any disclaimer, the term of this patent is extended or adjusted under 35 U.S.C. 154(b) by 59 days.

(21) Appl. No.: 10/854,750

(22) Filed: May 27, 2004

(65) Prior Publication Data

US 2005/0142300 A1 Jun. 30, 2005

(30) Foreign Application Priority Data

May 27, 2003 (EP) .................................. 03011898

(51) Int. Cl.$^7$ ....................... C09K 19/34; C09K 19/20; C09K 19/30; C07D 309/00; C07D 315/00
(52) U.S. Cl. ............. 428/1.1; 252/299.61; 252/299.63; 252/299.67; 549/356; 549/428
(58) Field of Search ............... 549/356, 428; 425/1.1; 252/299.61, 299.62, 299.63, 299.66, 252/299.67

(56) References Cited

U.S. PATENT DOCUMENTS

| | | | |
|---|---|---|---|
| 5,368,771 A | * | 11/1994 | Namekawa et al. ... 252/299.01 |
| 6,329,027 B1 | * | 12/2001 | Kondo et al. ................ 428/1.1 |
| 6,541,081 B1 | * | 4/2003 | Bremer et al. .............. 428/1.1 |
| 6,558,758 B1 | * | 5/2003 | Yanai et al. ................. 425/1.1 |
| 2004/0140452 A1 | * | 7/2004 | Hirschmann et al. .. 252/299.61 |

FOREIGN PATENT DOCUMENTS

DE 4132006 * 4/1993

* cited by examiner

Primary Examiner—Shean C. Wu
(74) Attorney, Agent, or Firm—Millen, White, Zelano & Branigan, P.C.

(57) ABSTRACT

Tetrahydropyran derivatives having at least one ester group (—CO—O—) and at least one group —CN, —NCS,

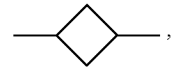

—F, —Cl, —OCHF$_2$, —OCF$_3$, —CF$_3$, —OCHFCF$_3$, —OCF$_2$CHFCF$_3$, SF$_5$, or —OCF$_2$CF$_3$; a process for preparing said tetrahydropyran derivatives, and the use of said tetrahydropyran derivatives as a component in a liquid crystal composition.

8 Claims, No Drawings

PYRANS AS LIQUID CRYSTALS

The invention relates to tetrahydropyran derivatives comprising at least one ester group (—CO—O) and at least one group selected from the group consisting of —CN, —NCS, —SF$_5$, —F, —Cl, —OCHF$_2$, —OCF$_3$, —CF$_3$, —OCF$_2$CHFCF$_3$, —OCHFCF$_3$, and —OCF$_2$CF$_3$.

In recent years, applicable fields of liquid crystals such as various kinds of display devices, electronic optical devices, liquid crystal sensors, etc. have markedly been enlarged, and accompanying this situation, liquid crystal compounds having various structures have been proposed. In liquid crystal materials particularly used for display devices, nematic liquid crystals are at present in mainstream, and a TN-type or a STN-type simple matrix system using the same and a TFT-type active matrix system in which a thin film transistor is provided to respective picture elements have been used.

It is known in the art to use tetrahydropyran derivatives as liquid crystal compounds.

DE-A 41 320 06 discloses heterocyclic compounds comprising a tetrahydropyran ring or a dioxane ring. The compounds show according to the specification of DE-A 41 320 06 a good solubility for other components of liquid crystalline compositions, a high positive dielectric anisotropy and an advantageous viscosity. However, the dielectric anisotropy of the compounds mentioned in DE-A 41 320 06 may be optimized. Further, in DE-A 41 320 06 tetrahydropyran derivatives comprising a combination of a tetrahydropyran ring and an ester group are not mentioned.

EP-A 0 967 261 discloses liquid crystal compounds having a negative dielectric anisotropy and liquid crystal compositions containing said liquid crystal compounds. The liquid crystal compounds disclosed in EP-A 0 967 261 contain a tetrahydropyran group and an aromatic ring which is substituted by at least one fluorine or chlorine atom. Compounds comprising a combination of a tetrahydropyran group and an ester group are not mentioned.

U.S. Pat. No. 4,818,431 discloses tetrahydropyran derivatives which are suitable for the preparation of stable liquid-crystal phases which have a strongly negative or positive dielectric anisotropy, and which show a comparatively low viscosity. However, the dielectric anisotropy of said compounds may be further optimized. Compounds comprising a combination of a tetrahydropyran group and an ester group are not mentioned.

U.S. Pat. No. 5,368,771 discloses optically active tetrahydropyran derivatives which can improve high speed response, and are available as compositional components for ferroelectric crystals which induce a large spontaneous polarization. Compounds comprising a tetrahydropyran group and an ester group are not mentioned.

Compounds suitable for liquid crystalline compositions comprising an ester group are also known in the art.

DE-A 100 53 896 discloses compounds suitable for liquid crystalline compositions comprising an ester group. However, compounds comprising a combination of an ester group and a tetrahydropyran group are not mentioned.

It is an object of the present invention to provide new tetrahydropyran derivatives which are suitable as components in liquid crystalline compositions, especially in nematic media having a positive dielectric anisotropy. It is a further object of the present invention to provide compounds having a good chemical stability and a distinct $\epsilon_{195}$ at a positive dielectric anisotropy, a low temperature dependence of the threshold voltage, and/or a low optical anisotropy. It is further an object of the present invention to provide compounds having a good solubility for other components of liquid crystal compositions and a high positive dielectric anisotropy and an advantageous value of viscosity.

These objects can be achieved by providing tetrahydropyran derivatives of formula I

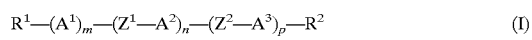

in which
R$^1$ is H, an alkyl group, which is unsubstituted or substituted by at least one halogen atom, having from 1 to 12 C atoms, it is also being possible for one or more non adjacent CH$_2$-groups to be independently replaced by —O—, —S—, —CO—, —CF$_2$—,

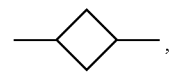

—CO—O, —O—CO—, or —CH=CH—, preferably unsubstituted alkyl group having from 1 to 12, preferably from 1 to 5, C atoms,
R$^2$ is —CN, —NCS, —SF$_5$—, —F, —Cl, —OCHF$_2$, —OCF$_3$, —CF$_3$, —OCF$_2$CHFCF$_3$—, —OCHFCF$_3$ or —OCF$_2$CF$_3$, preferably —F, —OCF$_3$, more preferably —F,
A$^1$, A$^2$, A$^3$ are each independently
  a) trans-1,4-cyclohexylene,
  b) tetrahydropyran-2,5-diyl,
  c) 1,4-phenylene, it is also being possible for one or more non adjacent CH-groups to be replaced by N, or CF,
  d) 1,4-bicyclo [2.2.2] octylen,
  e) naphthaline-2,6-diyl,
  f) decahydronaphthaline-2,6-diyl,
  g) 1,2,3,4-tetrahydronaphthtaline-2,6-diyl,
  h) 1,4-cyclohexenylene,
  it is also being possible for the groups listed under c), e), and g) to be substituted with —CN, —Cl, —F, —CF$_3$, or —OCF$_3$,
preferably A$^1$, A$^2$, A$^3$ are each independently
  a) trans-1,4-cyclohexylene,
  b) tetrahydropyran-2,5-diyl,
  c) 1,4-phenylene, it is also being possible for one or more non adjacent CH-groups to be replaced by N, or CF,
  it is also being possible for the groups listed under c) to be substituted with —CN, —Cl, —F, —CF$_3$, or —OCF$_3$, preferably —F, or —OCF$_3$, more preferably —F, with the proviso that one of the groups A$^1$, A$^2$, or A$^3$ is tetrahydropyran-2,5-diyl,
Z$^1$, Z$^2$ each is independently —CO—O—, —CH$_2$O—, —O—CH$_2$—, —CH$_2$CH$_2$—, —CH=CH—, —C≡C—, or a single bond, preferably —CO—O—, or a single bond, with the proviso that at least one of the groups Z$^1$ or Z$^2$ is —CO—O—,
m, n, p each is independently 0, 1, 2 or 3, preferably 0,1, or 2, but (m+n+p) is at least 2 and at most 4, preferably 3 or 4.

The compounds of formula I are useful as components in liquid crystalline compositions. It is especially possible to provide liquid crystalline compositions having large nematic areas, excellent chemical stability and excellent elastic features, a low temperature dependence of the threshold voltage, and/or low optical anisotropy. The compounds of formula I further show a high positive dielectric anisotropy and an advantageous value of viscosity as well as a large $\epsilon_\perp$ at positive dielectric anisotropy and a low temperature dependence of the threshold voltage. It was found, that the combination of an ester group and a tetrahydropyran group together with —CN, —NCS, —F, —Cl, —SF₅, —OCHF₂, —OCF₂CHFCF₃—, —OCF₃, —OCHFCF₃ or —OCF₂CF₃ as realized in the tetrahydropyran derivatives of the present invention of formula I results in compounds having balanced properties, especially a high dielectric anisotropy, a good hydrolytic stability and a good holding ratio.

The alkyl groups $R^1$ of the compounds of formula I may be linear or branched, preferably the alkyl groups are linear. More preferably $R^1$ is a linear alkyl group of the general formula $C_nH_{2n+1}$, wherein n is 1 to 10, preferably 1 to 7, more preferably $R^1$ is methyl, ethyl, n-propyl, n-butyl, n-pentyl, n-hexyl, or n-heptyl.

However, it is also possible that $R^1$ is a branched alkyl group, because of the better solubility of compounds of the formula I with branched alkyl groups in the generally used liquid crystalline basic materials, or especially as chiral dopants, when the compounds of the formula I having branched alkyl groups are optically active. Those branched alkyl groups contain usually not more than one branch. Preferred branched alkyl groups are isopropyl, 2-butyl (=1-methylpropyl), isobutyl (=2-methylpropyl), 2-methyl-butyl, isopentyl (=3-methylbutyl), 2-methylpentyl, or 3-methylpentyl.

Also included are besides the racemates of the tetrahydropyran derivatives their enantiomers—as the tetrahydropyran ring contains two chiral centers—and their resulting diastereomers derived from branched side chains represented by $R^1$.

In a preferred embodiment of the present invention tetrahydropyran derivatives are provided, wherein the group

 (I')

of the tetrahydropyran derivatives of formula I is

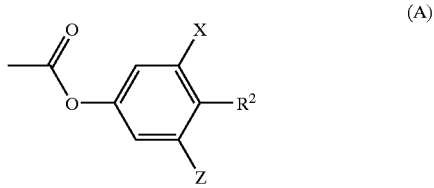 (A)

in which
X and Z each is H or F, and
$R^2$ is —F, —CF₃, —OCHFCF₃, —OCF₂CF₃ or —OCF₃, preferably —F or —OCF₃, preferably at least one of X and Z is —F or —OCF₃, more preferably X, Z, and $R^2$ are —F or one of X and Z is —F and $R^2$ is —OCF₃.

In this preferred tetrahydropyran derivatives of formula I comprising group A
$Z^2$ is —CO—O—,
$A^3$ is

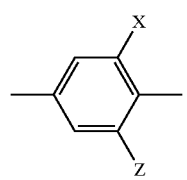

and
p is 1.

In a further embodiment of the present invention tetrahydropyran derivatives are provided, wherein the group

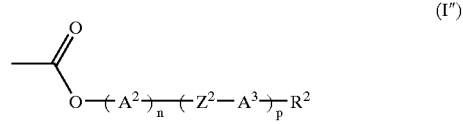 (I")

of the tetrahydropyran derivatives of formula I is

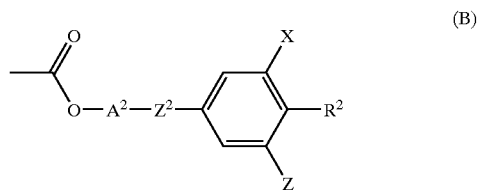 (B)

in which
$A^2$ is a phenylene group, optionally substituted by one or more F atoms,
X and Z each is H or —F, preferably at least one of X and Z is —F, and
$R^2$ is —F, —CF₃, —OCHFCF₃, —OCF₂CF₃ or —OCF₃, preferably —F or —OCF₃, preferably at least one of X and Z is —F or —OCF₃, more preferably X, Z, and $R^2$ are —F or one of X and Z is —F and $R^2$ is —OCF₃, and
$Z^2$ is —CO—O—, —CH₂O—, —O—CH₂—, —CH₂CH₂—, —CH=CH—, —C≡C—, or a single bond, preferably —CO—O, or a single bond.

In this preferred tetrahydropyran derivatives of formula I comprising group B
$Z^1$ is —CO—O—,
$A^3$ is

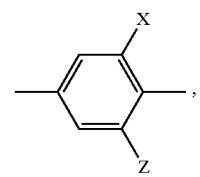

p is 1, and
n is 1.

The compounds of formula I are prepared by methods known in the art, as disclosed in literature, for example in Houben-Weyl, *Methoden der organischen Chemie*, Georg-Thieme-Verlag, Stuttgart, under reaction conditions which are known and useful for said reactions.

The starting materials used for the preparation of compounds of the formula I can be isolated or used in situ, which means that the starting materials are not isolated from the reaction mixture, but directly reacted to the compounds of formula I.

In the tetrahydropyran derivatives of formula I at least one of the groups $Z^1$ or $Z^2$ is an ester group, —CO—O—. In general the tetrahydropyran derivatives of formula I are therefore prepared—starting from two suitable fragments—by forming an ester group, —CO—O—, or, if $Z^1$ and $Z^2$ are —CO—O—, by forming of one of the ester groups. The ester group is formed by combining two fragments, wherein one fragment comprises a —COOH group and the other fragment comprises a —OH group. The fragments correspond to two parts of the tetrahydropyran derivatives of the formula I, which are linked by the ester group, —CO—O—. The two fragments itself are prepared by methods known in the art.

The concept mentioned above is shown in the following scheme 1 for a preferred tetrahydropyran compounds of formula I:

a)

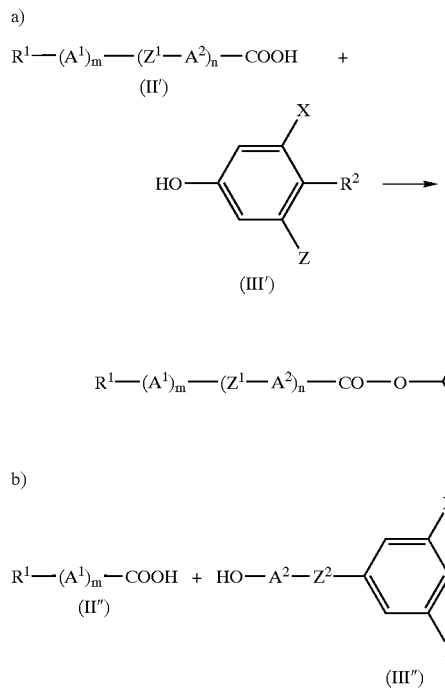

b)

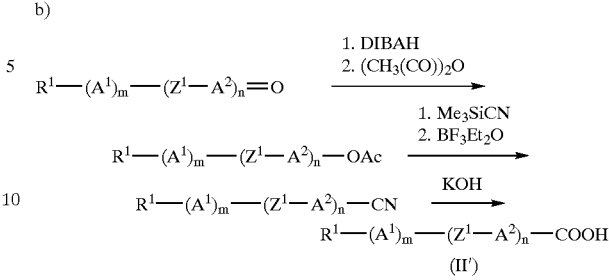

The symbols used in the scheme are already mentioned above.

The reaction conditions of the reactions mentioned in scheme 1 and scheme 2 as well as further details are known by a person skilled in the art.

In a further embodiment the present invention therefore relates to a process for preparing tetrahydropyran derivatives of formula I, wherein a carboxylic acid of formula II' respectively II"

respectively

is reacted with

respectively

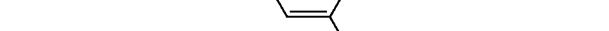

in which

R$^1$ is H, an alkyl group, which is unsubstituted or substituted by at least one halogen atom, having from 1 to 12 C atoms, it is also being possible for one or more non adjacent CH$_2$-groups to be independently replaced by —O—, —S—, CO—, —CF$_2$—,

—CO—O—, or —CH=CH—, preferably H, —F, —OCF$_3$, or an unsubstituted alkyl group having from 1 to 12, preferably from 1 to 5 C atoms, The symbols R$^1$, A$^1$, A$^2$, Z$^1$, Z$^2$, n, m, X, R$^2$ and Z are defined above.

The compounds of formulae II' and II" having a —COOH group are prepared by methods known in the art, for example by one of the methods shown in the following scheme 2, wherein the preparation of compounds of formula II' is shown. The preparation of compounds of formula II" is carried out by an analogous method:

a)

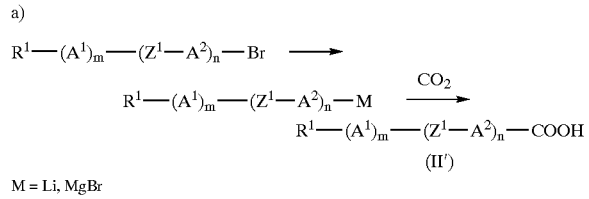

M = Li, MgBr $A^1$, $A^2$ are each independently
 a) trans-1,4-cyclohexylene,
 b) tetrahydropyran-2,5-diyl,
 c) 1,4-phenylene, it is also being possible for one or more non adjacent CH-groups to be replaced by N, or CF,
 d) 1,4-bicyclo[2.2.2]octylene, piperidine-2,5-diyl,
 e) naphthaline-2,6-diyl,
 f) decahydronaphthaline-2,6-diyl,
 g) 1,2,3,4-tetrahydronaphthaline-2,6-diyl,
 h) 1,4-cyclohexenylen,
 it is also being possible for the groups listed under c), e) and g) to be substituted with —CN, —Cl, —F, —CF$_3$, or —OCF$_3$,
 preferably $A^1$ and $A^2$ are each independently
 a) trans-1,4-cyclohexylene,
 b) tetrahydropyran-2,5-diyl,
 c) 1,4-phenylen, it is also being possible for one or more non adjacent CH-groups to be replaced by N, or CF,
 it is also being possible for the group listed under c) to be substituted with —CN, —Cl, —F, —CF$_3$, or —OCF$_3$, with the proviso that one of the groups $A^1$ or $A^2$ is tetrahydropyran-2,5-diyl,
$Z^1$ is —CO—O—, —CH$_2$O—, —O—CH$_2$—, —CH$_2$CH$_2$—, —CH=CH—, —C≡C—, or a single bond, preferably —CO—O—, or a single bond,
m, n each is independently 0, 1, 2, or 3, preferably 0, 1, or 2, but (m+n) is at least 1 and at most 3, preferably 2 or 3,
X and Z each is H or F, and
$R^2$ is —F, —CF$_3$, —OCHFCF$_3$, —OCF$_2$CF$_3$ or —OCF$_3$, preferably —F or —OCF$_3$, preferably at least one of X and Z is —F or —OCF$_3$, more preferably X, Z, and $R^2$ are —F or one of X and Z is —F and $R^2$ is —OCF$_3$.

The tetrahydropyran derivatives of formula I of the present invention are useful as components in liquid crystal compositions.

In a further embodiment the present invention therefore relates to the use of a tetrahydropyran derivative of formula I of the present invention as a component in a liquid crystal composition. The compounds of the present invention are especially useful in nematic liquid crystal compositions, especially in nematic liquid crystal compositions having a positive dielectric anisotropy. By using the tetrahydropyran derivatives of formula I of the present invention as components in liquid crystal compositions liquid crystal compositions having a broad nematic area, excellent chemical stability, excellent elastic properties, large ε⊥ at a positive dielectric anisotropy, low temperature dependence of the threshold voltage and/or low optical anisotropy are provided. Further, the tetrahydropyran derivatives of the present invention show a good solubility for other components of liquid crystal compositions, a high positive dielectric anisotropy and an advantageous value of viscosity.

In a further embodiment of the present invention a liquid crystal composition is provided comprising at least two components including at least one tetrahydropyran derivative of formula I of the present invention.

The liquid crystal compositions of the present invention preferably contain at least one tetrahydropyran derivative of formula I of the present invention and in general 2 to 40, preferably 4 to 30, more preferably 7 to 25 further components. These further components are preferably selected from nematic or nematogenic (monotropic or isotropic) compounds, especially compounds of the classes of biphenyl, terphenyl, phenylbenzoate or cyclohexylbenzoate, cyclohexane carboxylic acid phenyl ester or cyclohexane carboxylic acid cyclohexyl ester, phenyl ester or cyclo hexyl ester of cyclohexyl benzoic acid, phenyl ester or cyclohexyl ester of cyclohexyl cyclohexane carboxylic acid, cyclohexyl phenyl ester of benzoic acid, cyclohexyl phenyl ester of cyclohexane carboxylic acid, cyclohexyl phenyl ester of cyclohexyl cyclohexane carboxylic acid, phenylcyclohexane, cyclohexylbiphenyl, phenylcyclohexyl cyclohexane, cyclohexyl cyclohexane, cyclohexyl cyclo hexene, cyclohexyl cyclohexyl cyclohexene, 1,4-bis-cyclohexylbenzene, 4,4-bis-cyclohexylbiphenyl, phenylpyrimidine, cyclohexylpyrimidine, phenyl-pyridine, cyclohexylpyridine, phenyldioxane, cyclohexyldioxane, phenyl-1,3-dithiane, cyclohexyl-1,3-ditiane, 1,2-diphenylethane 1,2-dicyclohexylethylene, 1-phenyl-2-cyclhexylethane, 1-cyclohexyl-2-(4-phenylcyclohexyl)-ethane, 1-cyclohexyl-2-biphenylylethane, 1-phenyl-2-cyclohexylphenylethane and tolane. The 1,4-phenylene groups of said compounds may be fluorinated.

Instead of the ester-carboxylic linkage (—CO—O—) between a cyclohexyl ring or phenyl ring and a phenyl ring in the ester derivatives mentioned above, linkages with the structures —CF$_2$O—, —CH$_2$—CH$_2$—, —CH=CH—, —C≡C—, —CF=CF—, —CF$_2$—CF$_2$— may be incorporated.

The most preferred further components of the liquid crystal compositions of the present invention are characterized by the formulae A, B, C, D, E, and F:

 (A)

 (B)

 (C)

 (D)

 (E)

 (F)

wherein
L, E are each independently selected from the group consisting of —Phe—, —Cyc—, —Phe—Phe—, —Cyc—Phe—, —Cyc—Cyc—, —Pyr—, —Dio—, —G—Phe—, and —G—Cyc—; as well as the mirror images of the groups mentioned before, wherein Phe is unsubstituted 1,4-phenylene or substituted 1,4-phenylene, which is substituted by —F, Cyc is trans-1,4-cyclohexylene or 1,4-cyclohexenylene, Pyr is pyrimidine-2,5-diyl or pyridine-2,5-diyl, Dio is 1,3-dioxane-2,5-diyl, and G is 2-(trans-1,4-cyclohexyl)-ethyl, pyrimidine-2,5-diyl, pyridine-2,5-diyl, or 1,3-dioxane-2,5-diyl; preferably at least one of the groups L and E is Cyc, Phe, or Pyr; more preferably E is Cyc, Phe or —Cyc—Phe—.

In a preferred embodiment of the present invention the liquid crystal compositions of the present invention contain one or more components selected from the group consisting of formulae A, B, C, D, E, and F, wherein L and E are selected from the group consisting of Cyc, Phe, and Pyr and at the same time one or more components selected from compounds of formulae A, B, C, D, E, and F, wherein one of the groups L and E is selected from the group consisting of Cyc, Phe, and Pyr, and the other group is selected from the group consisting of —Phe—Phe—, —Cyc—Phe—, —Cyc—Cyc—, —G—Phe—, and —G—Cyc, and optionally one or more components selected from the group consisting of the compounds of formulae A, B, C, D, E, and F, wherein the groups L and E are selected from the group consisting of —Cyc—Phe—, —Cyc—Phe—, and —G—Cyc.

R' and R" each are independently of each other alkyl, alkenyl, alkoxy, alkenyloxy or alkanoyloxy having from 1 to 8 carbon atoms, preferably R' and R" are different and at least one of R' and R" is alkyl or alkenyl (group 1).

In a further embodiment R' is alkyl, alkenyl, alkoxy, alkenyloxy, or alkanoyloxy having from 1 to 8 carbon atoms, preferably alkyl or alkenyl, and R" is —CN, —CF$_3$, —OCF$_3$, —F, Cl, or NCS, preferably —F, —Cl, —OCF$_3$, or —OCF$_3$ (group 2).

In general further combinations of the substituents mentioned in the compounds of formulae A, B, C, D, E, and F are possible. Many of the compounds mentioned above or mixtures of said compounds are buyable. All compounds mentioned above are preparable by methods known in the art or analogous methods which are known by a person skilled in the art.

The liquid crystal compositions of the present invention preferably comprise components of group 1 of the compounds as mentioned above as well as components of group 2 of the compounds as mentioned above. More preferably, the liquid crystal compositions of the present invention comprise 20 to 90% by weight, preferably 30 to 90% by weight of compounds of group 1 and 10 to 80% by weight, preferably 10 to 50% by weight of compounds of group 2, and at least one tetrahydropyran derivative of formula I of the present invention, wherein the sum of the parts of compounds of group 1, compounds of group 2 and tetrahydropyran derivatives of formula I of the present invention is 100% by weight.

Preferably the liquid crystal compositions of the present invention comprise 1 to 40% weight, more preferably 5 to 30% by weight of the tetrahydropyran derivatives of formula I of the present invention.

In a further embodiment of the present invention the liquid crystal compositions of the present invention comprise more than 40% by weight, preferably 45 to 90% by weight of the tetrahydropyran derivatives of formula I of the present invention.

The liquid crystal compositions of the present invention preferably comprise three, four, or five different tetrahydropyran derivatives of formula I of the present invention.

The liquid crystal compositions of the present invention are prepared in a manner known per se. In general, the components are solved in each other, preferably at elevated temperature.

As a rule, the desired amount of the components used in the smaller amount is dissolved in the components making up the main component, expediently at elevated temperature. It is also possible to mix solutions of the components in an organic solvent, for example in acetone, chloroform or methanol, and to remove the solvent again after thorough mixing, for example by distillation.

The liquid crystalline phases obtained with the liquid crystal compositions of the present invention may be modified so that they are suitable for use in all liquid crystal display devices known in the art.

Suitable additives are known by a person skilled in the art and are described in literature (see for example H. Kelker/R. Hatz, *Handbook of Liquid Crystals*, Verlag Chemie, Weinheim, 1980). Suitable additives are for example pleochroitic dyes for the preparation of colored guest-host-systems, or substances for changing the dielectric anisotropy, the viscosity and/or the orientation of the nematic phases or stabilizers which prevent the oxidative influence of O$_2$ or destruction by radicals formed by light or otherwise.

Liquid crystal mixtures which contain one or more tetrahydropyran derivatives of formula I of the present invention and very particularly liquid crystal mixtures additionally comprising components or component mixtures as mentioned above have advantageous properties and correspond to the requirements described at the beginning. The tetrahydropyran derivatives of formula I of the present invention show a very high dielectric anisotropy ($\Delta\epsilon$). That compounds are very useful for the preparation of liquid crystal mixtures which are employed in order to achieve low threshold voltages. $\Delta n$ of the liquid crystal mixtures can be influenced by the proper selection of the components, as $\Delta n$ is mainly governed by the $\pi$-electrons present in the structural ring elements, linkage elements, and endgroup elements.

A further embodiment of the present invention relates to a liquid crystal display device constituted by the use of the liquid crystal compositions of the present invention.

Further, the present invention relates to an electro-optical display device constituted by the use of the liquid crystal composition of the present invention. These devices may be TN-cells (Schadt-Helfrich) or active matrix TFT-displays with high resolution.

The following examples are intended to illustrate the invention without limiting.

The symbols have the following meaning:
K: crystalline solid state,
S: smectic phase (the index characterizes the phase type),
N: nematic phase,
I: isotrop phase.

The number between two symbols gives the transition temperature in degrees Celsius.

The percentage data given are percentages by weight.

EXAMPLES

Example 1

Synthesis of the alkyl tetrahydropyran carboxylic acid 5

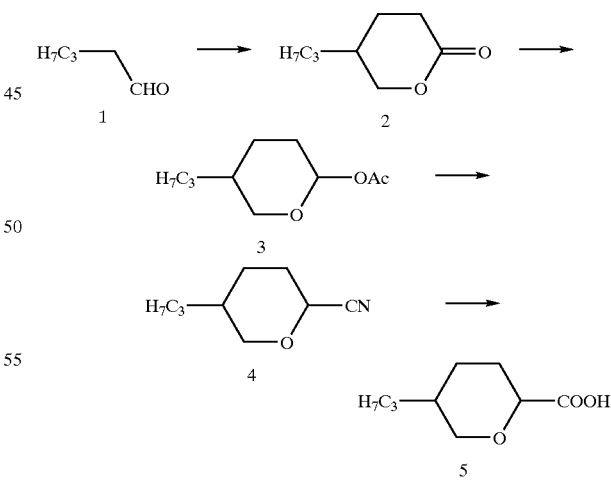

A mixture of 500 mmol pentan-1-al (1), 700 mmol methacrylate, 50 mmol trimethylsilyldiemethylamine and 300 mmol acetonitril are heated under reflux for 18 h. Acetonitril and silanes are removed in vacuo. 2.5 mmol acetic acid are then added and it was stirred for 18 h at 50° C. 2 N NaOH were added for neutralization and the reaction mixture was diluted with 3 l brine. The organic phase was separated and washed with brine and dried over Na$_2$SO$_4$. 11 isopropanol and subsequently 250 mmol sodium borhydride were added and it was stirred for 18 h. The mixture was worked up (aqueous), and the organic phase was washed with brine for two times and dried with Na$_2$SO$_4$. The crude alcohol was cooked with 11 toluence and 1 g toluence sulfonic acid at a water separator until the reaction was completed. The solution was washed until neutrality and subsequently purified by distillation. Yield of lacton (2): 35% of a liquid with intensive woodruff smell.

To a solution of 200 mmol 2 in 400 ml THF 200 mmol DIBAH were added at −70° C. The reaction mixture was warmed up to room temperature, 500 ml H$_2$O were added, the reaction mixture was acidified with 2N HCL, and worked up (aqueous) as known per se.

The crude lactol was dissolved in 300 ml pyridine and at 0° C. 100 ml acetic anhydride were added dropwise. It was stirred 18 h at room temperature and the reaction mixture was worked up (aqueous) as known per se. The crude product was distilled in vacuo. Yield of 3: 72%.

To a solution of 100 mmol 3 in 300 ml CH$_2$Cl$_2$ have been added first 110 mmol Me$_3$SiCN at −70° C., then BF$_3$Et$_2$O was added dropwise. The reaction mixture was warmed up to room temperature and worked up (aqueous) in a manner known per se. The product was purified by distillation in vacuo. Yield of 4: 84%.

50 mmol 4 were heated under reflux together with 100 mmol KOH, dissolved in 100 ml ethelene glycol until formation of ammonia. The solution was cooled and acidified with H$_2$SO$_4$ (20%). The product was extracted with diethyl ether, washed with water and evaporated until dryness. The crude acid was purified by distillation in vacuo. Yield of 5: 73%.

Example 2

Synthesis of the tetrahydropyran derivative 8

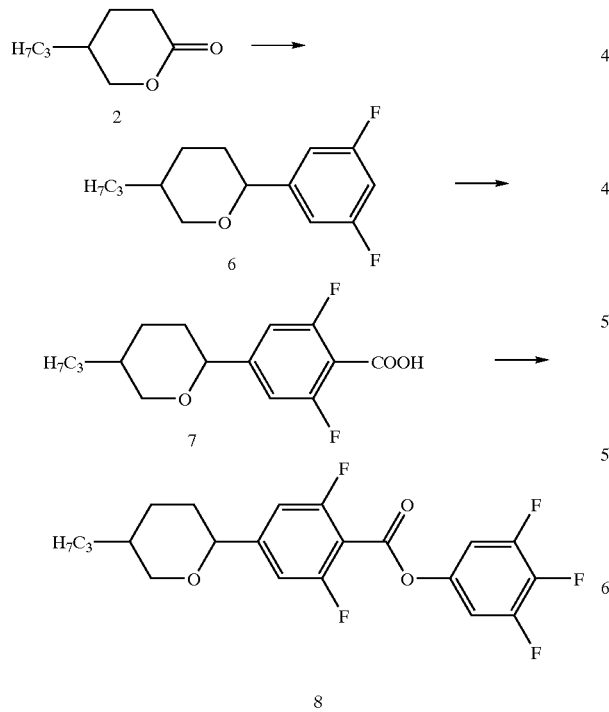

To a solution of 105 mmol 3,5-difluorobromobenzene in 100 ml diethylether 105 mmol n-BuLi (15% in hexanes) were added dropwise at −70° C. After 1 h 100 mmol 2 were added dropwise. The reaction mixture was stirred at −70° C. for 2 h and then warmed up to −10° C. The solution was worked up (aqueous) in a manner known per se. The crude intermediate was dissolved in 150 ml CH$_2$Cl$_2$ and cooled to −75° C. To said solution first 170 mmol BF$_3$-etherate and subsequently 170 mmol triethylsilane were added. After 2 h it was warmed up to −10° C. and worked up (aqueous) in a manner known per se. The crude product was purified by chromatography (silica gel; heptane/toluene 3:2). Yield of 6: 62%.

To 50 mmol 6 dissolved in 200 ml THF 55 mmol n-BuLi (14% in hexanes) were added at −70° C. It was stirred for 1 h and subsequently a large excess of dry CO$_2$ was introduced into the reaction mixture. The reaction mixture was warmed up to room temperature, water was added and it was acidified with 2N HCl. The product was extracted with either and worked up (aqueous) in a manner known per se and purified by crystallization from heptane at −20° C. Yield of 7: 82%.

A mixture of 10 mmol 7, 10 mmol 3,4,5-trifluorophenol, 10 mmol DCC, and 100 ml CH$_2$Cl$_2$ was stirred at room temperature for 18 h. The reaction mixture was filtered from precipitated urea, the solvent was removed and the product was purified by crystallization from heptane at −20° C. Yield of 8: 78%.

In the same manner as mentioned above the following compounds have been prepared:

9:

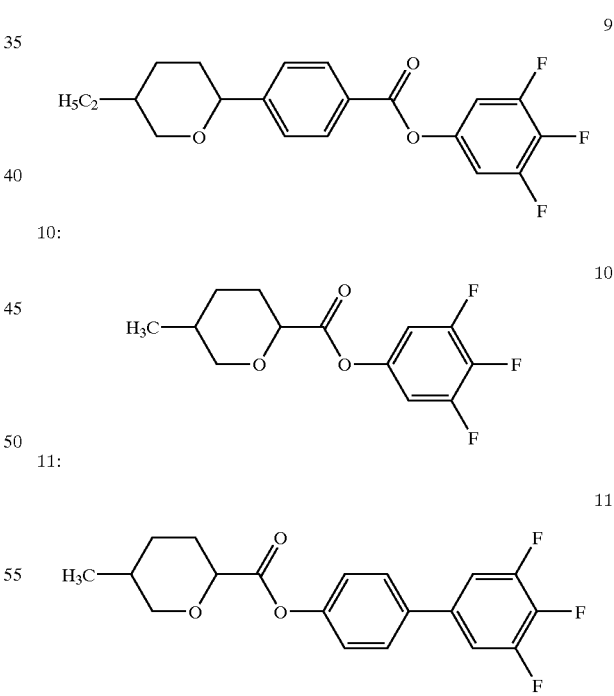

The tetrahydropyran derivatives of the present invention show a very good combination of dielectric anisotropy Δε and viscosity. In the following examples the compounds of the present invention are compared with similar compounds, which do not comprise a combination of a tetrahydropyran group and an ester group:

Example A (Inventive)

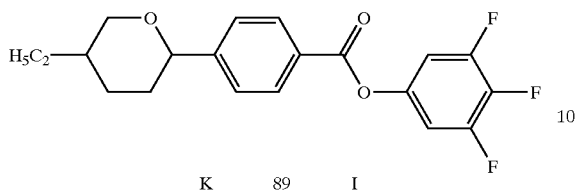

K 89 I

| Δε | 29.7 | ε⊥ | 8.2 |
|---|---|---|---|
| Δn | 0.1070 | n0 | 1.4972 |

Example B (Comparison Example)

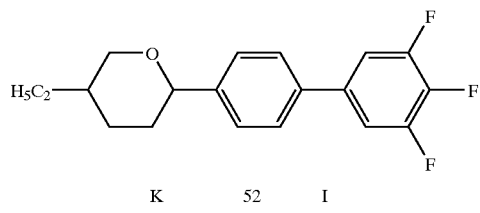

K 52 I

| Δε | 14.5 | ε⊥ | 7.1 |
|---|---|---|---|
| Δn | 0.1159 | n0 | 1.5031 |

Example C (Comparison Example; DE-A 100 53 896)

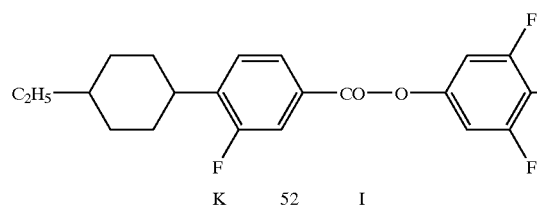

K 52 I

| Δε | 14.67 |
|---|---|
| Δn | 0.12 |

The entire disclosure of all applications, patents and publications, cited herein and of corresponding European application No. 03011898.8, filed May 27, 2003, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A tetrahydropyran compound of formula I $$R^1-(A^1)_m-(Z^1-A^2)_n-(Z^2-A^3)_p-R^2 \quad (I)$$

in which
$R^1$ is H, or an alkyl group having 1 to 12 C atoms, which is unsubstituted or substituted by at least one halogen atom, in which one or more non adjacent $CH_2$-groups are optionally, each independently, replaced by —O—, —S—, —CO—, —CF$_2$—,

—CO—O—, —O—CO—, or —CH=CH—,
$R^2$ is —CN, —NCS, —F, —SF$_5$, —Cl, —OCHF$_2$, —OCF$_3$, —CF$_3$, —OCF$_2$CHFCF$_3$, —OCHFCF$_3$, or —OCF$_2$CF$_3$,
$A^1$, $A^2$, $A^3$ are, each independently,
  a) trans-1,4-cyclohexylene,
  b) tetrahydropyran-2,5-diyl,
  c) 1,4-phenylene, in which one or more non adjacent CH-groups are optionally, each independently, replaced by N, or CF,
  d) 1,4-bicyclo[2.2.2]octylen,
  e) naphthaline-2,6-diyl,
  f) decahydronaphthaline-2,6-diyl,
  g) 1,2,3,4-tetrahydronaphthtaline-2,6-diyl, or
  h) 1,4-cyclohexenylene,
  wherein the groups listed under c), e), and g) are optionally substituted with —CN, —Cl, —F, —CF$_3$, and/or —OCF$_3$, and
  wherein at least one of the groups $A^1$, $A^2$, or $A^3$ is tetrahydropyran-2,5-diyl,
$Z^1$ $Z^2$ are, each independently, —CO—O, —CH$_2$O—, —O—CH$_2$—, —CH$_2$CH$_2$—, —CH=CH—, —C≡C—, or a single bond,
  wherein at least one of the groups $Z^1$ or $Z^2$ is —CO—O—, and
m, n, p are, each independently, 0, 1, 2 or 3, and m+n+p is 2, 3 or 4.

2. A tetrahydropyran compound of claim 1, wherein n, m, and p are, each independently, 0 or 1, and m+n+p is 3 or 4.

3. A tetrahydropyran compound of claim 1, wherein the group $$-(Z^2-A^3)_p-R^2 \quad (I')$$

of the tetrahydropyran compound of formula I is

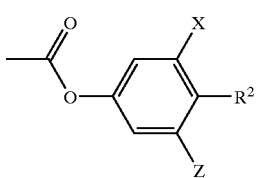

in which
X and Z are, each independently, H or F, and
$R^2$ is —F, —CF$_3$, —OCHFCF$_3$, —OCF$_2$CF$_3$ or —OCF$_3$.

4. A tetrahydropyran compound of claim 1, wherein the group

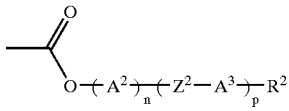 (I″)

of the tetrahydropyran compound of formula I is

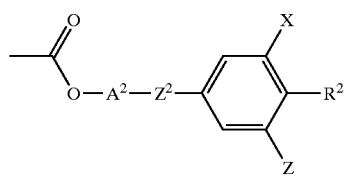 (B)

in which $A^2$ is a phenylene group, optionally substituted by one or more F atoms, X and Z are, each independently, H or —F, $R^2$ is —F, —$CF_3$, —$OCHFCF_2$, —$OCF_2CF_3$ or —$OCF_3$, and $Z^2$ is —CO—O—, —$CH_2$O—, —O—$CH_2$—, —$CH_2CH_2$—, —CH=CH—, —C≡C—, or a single bond.

5. A process for preparing a tetrahydropyran derivative of formula I of claim 1, comprising reacting a carboxylic acid of formula II' with a compound of formula III' or reacting a carboxylic acid of formula II″ with a compounds of formula III″

 (II')

 (II″)

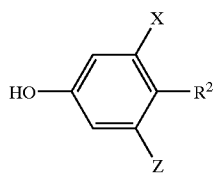 (III')

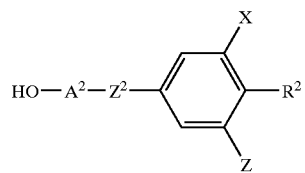 (III″)

in which $R^1$ is H, or an alkyl group having 1 to 12 C atoms, which is unsubstituted or substituted by at least one halogen atom, in which one or more non adjacent $CH_2$-groups are optionally, each independently, replaced by —O, —S—, CO—, —$CF_2$—,

—CO—O—, or —CH=CH—, $A^1$, $A^2$ are, each independently,
a) trans-1,4-cyclohexylene,
b) tetrahydropyran-2,5-diyl,
c) 1,4-phenylene, which is one or more non adjacent CH-groups are optionally, each independently, replaced by N, or CF,
d) 1,4-bicyclo[2.2.2]octylene, piperidine-2,5-diyl,
e) naphthaline-2,6-diyl,
f) decahydronaphthaline-2,6-diyl,
g) 1,2,3,4-tetrahydronaphthaline-2,6-diyl, or
h) 1,4-cyclohexenylen,
wherein the groups listed under c), e) and g) are optionally substituted with —CN, —Cl, —F, —$CF_3$, and/or —$OCF_3$, and
wherein at least one of the groups $A^1$ or $A^2$ is tetrahydropyran-2,5-diyl, $Z^1$ is —CO—O, —$CH_2$O—, —O—$CH_2$—, —$CH_2CH_2$—, —CH=CH—, —C≡C—, or a single bond, m, n are, each independently, 0, 1, 2, or 3, and m+n is 1, 2, or 3, X and Z are, each independently, H or F, and $R^2$ is —F, —$CF_3$, —$OCHFCF_2$, —$OCF_2CF_3$ or —$OCF_3$.

6. A liquid crystal composition comprising a compound according to claim 1.

7. A liquid crystal display comprising a liquid crystal composition according to claim 6.

8. An electro-optical display device comprising a liquid crystal composition according to claim 6.

* * * * *